United States Patent [19]

Nakagawa et al.

[11] 4,162,126
[45] Jul. 24, 1979

[54] SURFACE DETECT TEST APPARATUS

[75] Inventors: Yasuo Nakagawa, Yokohama; Toshimitsu Hamada, Tokyo, both of Japan

[73] Assignee: Hitachi, Ltd., Japan

[21] Appl. No.: 859,206

[22] Filed: Dec. 9, 1977

[30] Foreign Application Priority Data

Dec. 10, 1976 [JP] Japan ............................. 51-147764
Dec. 24, 1976 [JP] Japan ............................. 51-154882

[51] Int. Cl.$^2$ .......................................... G01N 21/48
[52] U.S. Cl. .................................. 356/237; 250/563; 250/572; 356/430; 356/446
[58] Field of Search ............... 356/120, 200, 210, 237; 250/562, 563, 572

[56] References Cited

U.S. PATENT DOCUMENTS 3,782,836  1/1974  Fey et al. ...................... 356/237 X

OTHER PUBLICATIONS

Sommer et al., "Detection and Measurement of Epitaxial Spikes", *IBM Technical Disclosure Bulletin*, vol. 13, No. 11, p. 3496, Apr. 1971.

*Primary Examiner*—Conrad J. Clark
*Assistant Examiner*—Matthew W. Koren
*Attorney, Agent, or Firm*—Craig and Antonelli

[57] ABSTRACT

Apparatus and method for testing surface defect on an object are disclosed, which comprise an illumination means for illuminating collimated lights onto a surface of the object obliquely to the surface and from two symmetrical directions, a sensor composed of a TV camera or a linear image sensor for sensing diffused reflected lights from the surface of the object in the direction perpendicular to the surface, a classification means for discriminating the sensed image signal by a threshold level which is higher than an average level of the image signal and a threshold level which is lower than the average level to determine the surface defect pattern as a broken cavity pattern or a pit or crack pattern by the discriminated signals, and a discrimination means for calculating $L^2-4\pi S$, where S is an area of the defect and L is a length of the contour, when signal discriminated by the lower threshold level is produced to discriminate the pit pattern and the crack pattern by determining whether $L^2-4\pi S$ exceeds a predetermined value or not. In this manner, the defects that exist on the surface of the object can be classified and evaluated.

3 Claims, 28 Drawing Figures

SURFACE DEFECT TEST APPARATUS

LIST OF PRIOR ART REFERENCES (37 CFR 1.56(a))

The following references are cited to show the state of the art:

The article "Automatic Inspection of Surface Defect of Function Component" disclosed in pages 117–124 of Japanese Journal "Mechanical Automation" Vol. 5 No. 12 1973.

The article "Automatic Inspection of Fuel-element Pellets" disclosed in "Metology and Inspection" Autumn 1969 published by Vernon Instrument Co. Ltd.

BACKGROUND OF THE INVENTION

The present invention relates to a surface defect test apparatus for inspecting a defect on a surface of a rod-shaped object, although not restrictive, such as a mechanical part e.g. bearing roller which is casted, sintered or machined or an uranium pellet for nuclear fuel, said defect particularly influencing to performance and property of the object.

An example of prior art surface defect test apparatus is shown in FIG. 1, which is a defect test apparatus utilizing a photo-electric conversion element such as a photo-transistor. (The article "Automatic Inspection of Surface Defect of Function Component" disclosed in pages 117–124 of Japanese Journal "Mechanical Automation" Vol. 5 No. 12 1973). In FIG. 1, light emitted from a light source 1 is focused by a lens 3 and directed onto a surface 5 of an object, in a spot, from an oblique direction a reflecting light therefrom is focused on a photo-electric conversion element 2 through a lens 4 in a normal reflection direction, or a diffused reflection light is focused on a photo-electric conversion element 2' through a lens 4' in a diffused reflection direction, depending on the surface condition of the illuminated portion of the object. A detection head comprising the light source 1, the photo-electric conversion element 2 or 2', the lens 3 and the lens 4 or 4' is moved to scan the surface 5 of the object to test the surface 5.

FIG. 2a to FIG. 2g show test results. FIG. 2a shows a sectional view of the surface 5 of the object, in which, by way of example, numeral 6 denotes a large defect and numeral 7 denotes a small defect. It is assumed that the light spot is scanned in the direction of an arrow. When the defects 6 and 7 exist on the surface 5 of the object, the reflected light therefrom is scattered so that the amount of reflected light directed to the photo-electric conversion element 2 arranged in the direction of normal reflection decreases and the light directed to the lens 3 is not focused into a complete spot. Accordingly, depending on the size of defect, an output level of a detected signal 8 with respect to time t derived from the photo-electric conversion element 2 changes as shown in FIG. 2b. When the detected signal 8 is discriminated by two threshold levels 9 and 10, di-value signals 11 and 12 shown in FIG. 2c and FIG. 2d are produced. When the diffused reflection light is received by the photo-electric conversion element 2' arranged directly above the illuminated portion, a detected signal 8' as shown in FIG. 2e is produced, which signal is inverse to the detected signal shown in FIG. 2b in their output levels (brightness level). When the detected signal 8' is discriminated by two threshold levels 9' and 10', di-value signals 11' and 12' as shown in FIG. 2f and FIG. 2g are produced.

Thus, the signals 11 and 11' which are discriminated by higher threshold levels 9 and 9' each has two peaks corresponding to the large defect 6 and the small defect 7 while the signals 12 and 12' which are discriminated by the lower threshold levels 10 and 10' each has one peak corresponding to the large defect 6. Accordingly, by comparing the signals 11 and 11' with the signals 12 and 12', the size of the defect can be determined.

However, in the prior art appatatus of this type in which the defect is detected by sensing the normal reflection light or diffused reflection light from the surface 5 of the object by the photo-electric conversion element 2 or 2', it is possible to determine the size of the defect on the surface of the object but it is difficult to classify and evaluate various defects such as broken cavity, crack and pinhole (pit) by sensing the normal reflection light and the diffused reflection light.

As an alternative, it is known to inspect the defect of the object by an air gauge. (The article "Automatic Inspection of Fuel element Pellets" disclosed in "Metology and Inspection" Autumn 1969 published by Vernon Instrument Co. Ltd.). Since this system has a low resolution power, it can detect and evaluate only large defects but it cannot classify and evaluate various small defects such as broken cavity, crack and pinhole (pit). It also requires longer test time.

SUMMARY OF THE INVENTION

It is a primary object of the present invention to provide a surface defect test apparatus which can rapidly classify and evaluate the defects on the surface of the object including broken cavity, crack and pinhole (pit).

In accordance with the present invention, collimated light rays are illuminated onto the surface of the object from at least two opposite and oblique directions and the diffused reflection light from the surface is sensed in the direction perpendicular to the surface of the object so that the signal corresponding to the surface condition is sensed. This sensed signal is discriminated by a threshold level $V_a$ which is higher than an average level of the sensed signal, and if an output is detected, the defect pattern is classified as the broken cavity pattern. On the other hand, the sensed signal is discriminated by a threshold level $V_b$ which is lower than the average level and if an output is detected, the defect pattern is classified as the pit or crack pattern. Further the pit or crack pattern is classified onto one of the pit pattern and the crack pattern by the relation between the contour and the length of the pattern.

DESCRIPTION OF THE PREFERRED EMBODIMENTS

Figure 1:
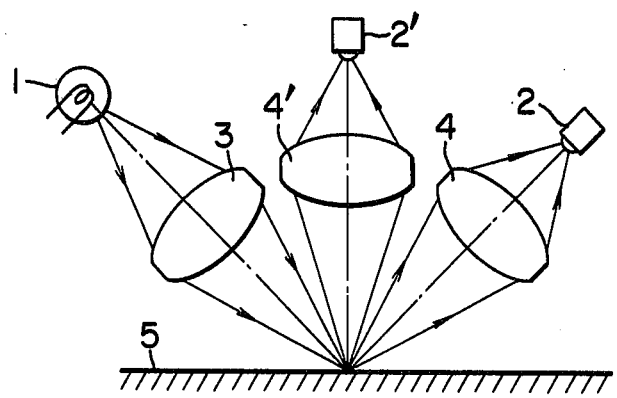
FIG. 1 shows a schematic construction of a prior art surface defect test equipment.
Figure 3:
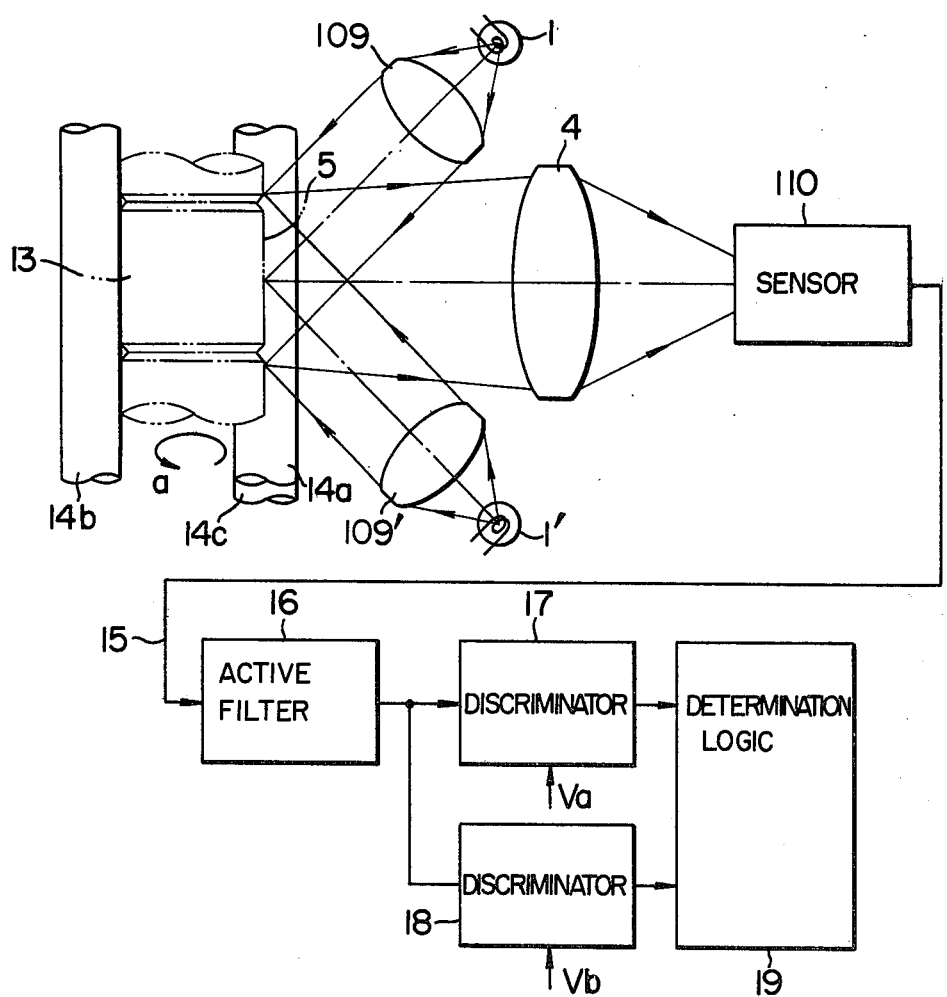
FIG. 3 shows a schematic construction of one embodiment of a surface defect test apparatus of the present invention.
Figures 2A, 2B, 2C, 2D, 2E, 2F, 2G:
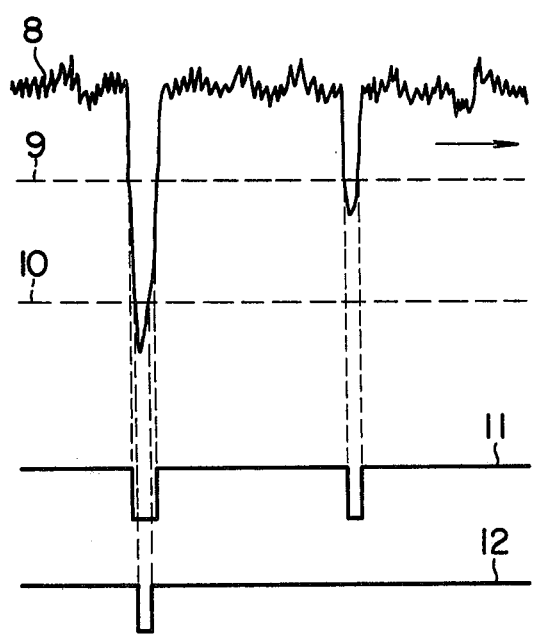
FIG. 2a to FIG. 2g show charts for explaining the test operation by the apparatus shown in FIG. 1.

FIG. 3 is a block diagram showing one embodiment of the surface defect test apparatus of the present invention. In FIG. 3, the same reference numerals are applied to like parts as in FIG. 1. Numerals 1 and 1' denote illumination light sources, and 109 and 109' denote illumination lenses which function to direct collimated light rays having rectangular cross-section to a surface 5 of an object 13 obliquely thereto from two opposite directions. The object 13 having the surface 5 is shaped in a cylinder shape, for example, and held by three rollers 14a, 14b and 14c to be rotated in the direction of an arrow a at a constant speed. (In FIG. 3, three objects 13 are arranged side by side between the three rollers.) Numeral 4 denotes an image lens which is large enough to cover the longitudinal width of each of the objects 13 and focuses an image of stripe surface area onto a sensor (image pickup device) 10, which may be any device that can detect diffused reflection light representative of the brightness of a predetermined unit area (or picture element) on the surface 5 of the object 13 and produce an output (image signal) in accordance with the amount of detected light. In the illustrated embodiment, image pickup elements such as TV cameras, linear image sensors or two-dimensional image sensors are arranged to simultaneously detect the diffused reflection lights of at least one longitudinal column of the object. Numeral 16 denotes an active filter which establishes level and frequency band of the image signal 15 derived from the sensor 110. Numerals 17 and 18 denote discrimination circuits and numeral 19 denotes a determination logic.

Figure 4A:
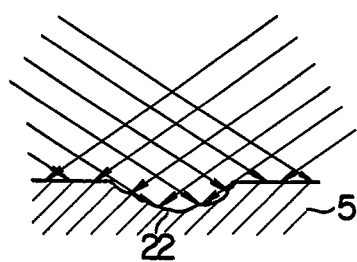
FIGS. 4a to 4b to FIGS. 7a to 7c show charts illustrating the relations between the sectional views of the defect patterns and the characteristic signals derived from the sensors of the present invention.
Figure 5A:
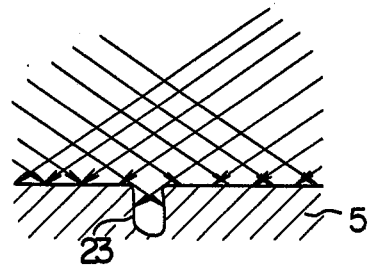
Figure 4B:
Figure 6A:
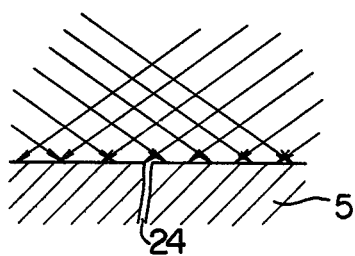
Figure 7A:
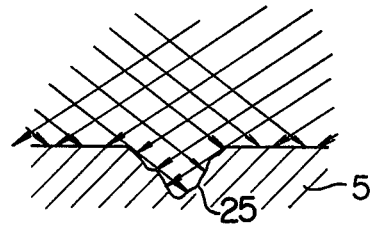
Figure 7B:
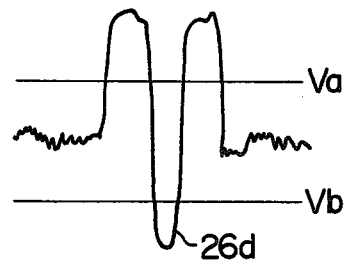
Figure 7C:
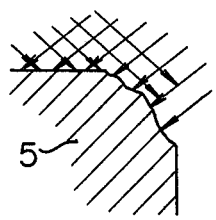

Stripes of collimated light from the two illumination devices comprising the light source 1 and the illumination lens 9, and the light source 1' and the illumination lens 9', respectively, are directed oppositely (that is, in upward and downward directions in the plane of drawing) and intersect with each other at 90° and directed onto the surface of the object at 45° respectively and scattered on the surface 5 of the object. The diffused reflection light is collected by the lens 4 arranged above the object 13 in the direction perpendicular to the surface of the object and converted to an electrical signal by the sensor 110. FIGS. 4a to 4b through FIGS. 7a to 7b illustrate the relations between the surface conditions and the image signals. The surface 5 of the object which has been fabricated by sintering, casting or rolling and mechanically finished generally includes defects such as broken cavities, pinholes, blowholes and cracks. FIG. 4a shows a broken cavity 22, FIG. 5a shows a defect 23 referred to pinhole, pit, hole or blowhole, FIG. 6a shows a crack 24 and FIGS. 7a and 7c show relatively deeply broken cavity 25. Hereinafter, the defects 22 and 25 as shown in FIGS. 4a, 7a and 7c are referred to broken cavities, the defect 23 as shown in FIG. 5a is referred to pit, and the defect 24 as shown in FIG. 6a is referred to crack.

In general, where the broken cavities 22 and 25 exist, the smoothness of the surface at those portions is rougher than the normally machined surface. As a result, an image signal 26a corresponding to the diffused reflection light is stronger (brighter) than that for the normal surface. Accordingly, when the image signal is discriminated by a threshold level $V_a$ which is higher than an average level, the broken cavities 22 and 25 can be detected.

Figure 5B:
Figure 6B:
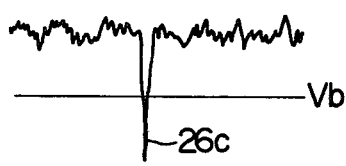

The pit 23 is a hole which has existed prior to the working of the object. At this portion, the illumination light does not reach the bottom of the hole and there is no diffused reflection light from that portion. Accordingly an image signal 26b corresponding to that portion is weak or dark as shown in FIG. 5b. Therefore, when the image signal is discriminated by a threshold level $V_b$ which is lower than the average level, the pit 23 can be detected. The same is true for the crack 24 and it can be detected by discriminating an image signal 26c by the threshold level $V_b$, as shown in FIG. 6b.

On the other hand, when the relatively deeply broken cavity exists, those portions on the surface of the cavity which are illuminated by the illumination light produce higher level image signal while those portions which are not illuminated produce lower level image signal, as shown in FIG. 7a. Accordingly, by discriminating an image signal 26d by the two threshold level, that is, the threshold level $V_a$ which is higher than the average level of the image signal and the threshold level $V_b$ which is lower than the average level, the deeply broken cavity can be detected.

Figure 8A:
FIGS. 8a to 8d show various defect patterns.
Figure 8B:
Figure 8C:
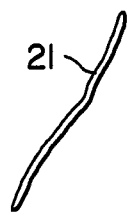
Figure 8D:
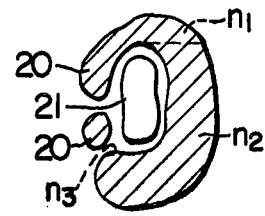

FIGS. 8a to 8d show the patterns of the discriminated image signals derived by scanning the surface 5 of the object 13. In FIG. 8a, numeral 20 denotes an area in which the image signal is higher than the threshold $V_a$ and 21 in FIG. 8b denotes an area in which the image signal does not exceed the threshold $V_b$. FIG. 8a shows the broken cavity, FIG. 8b shows the pit, FIG. 8c shows the crack and FIG. 8d shows the deeply broken cavity.

As shown in FIGS. 8a to 8d, since the image signals corresponding to the pit and the crack are always lower than the threshold $V_b$, the pit and the crack can be detected by discriminating the di-value signal derived from the discrimination circuit 17 shown in FIG. 3 by the determination logic 19. Around the broken cavity pattern which is discriminated by the threshold $V_b$, there always exists the broken cavity which is discriminated by the threshold $V_a$. Furthermore, the pit and the crack which are discriminated by the threshold $V_b$ are of generally circular shape and of linear shape, respectively.

From those characteristics, the determination logic 19 shown in FIG. 3 can classify and evaluate the broken cavity, pit and crack and further evaluate the quality of the surface of the object based on the above evaluation.

Figure 12:
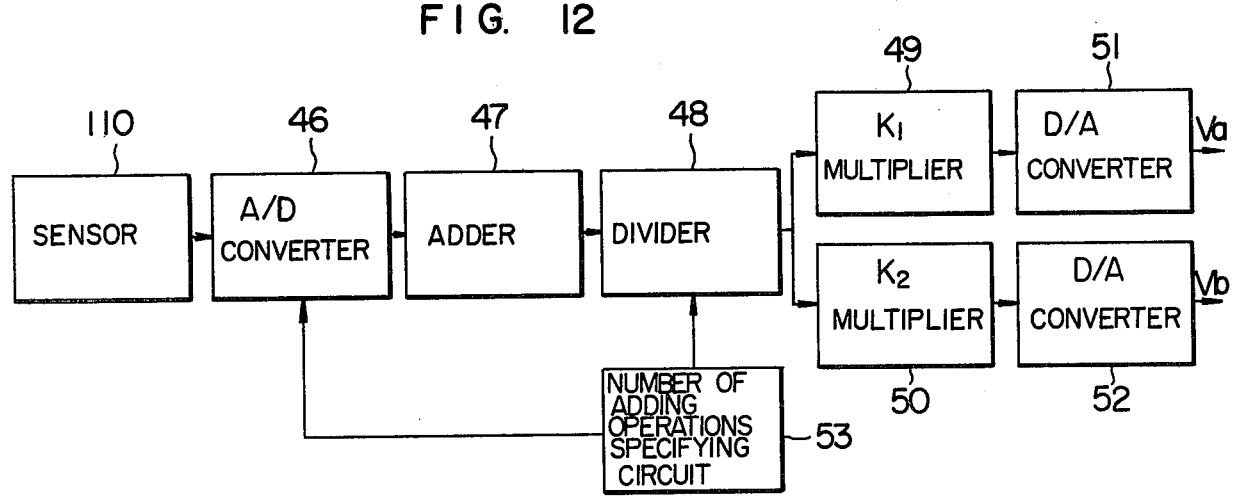
FIG. 12 shows a block diagram of a threshold determination circuit.

Referring to FIG. 12, a circuit for establishing the thresholds $V_a$ and $V_b$ is explained. Numeral 46 denotes an A/D converter which samples the image signal derived from the sensor 110 by predetermined clock pulses to convert the voltages of the image signal representative of the brightnesses at a plurality of points to digital signals. Numeral 47 denotes an adder circuit which sequentially adds the sampled digital signals from the A/D converter 46. Numeral 48 denotes a divider circuit, 49 denotes a multiplier circuit for multiplying a constant $K_1$ ($K_1 > 1$), 50 denotes a multiplier circuit for multiplying a constant $K_2$ ($K_2 < 1$), 51 and 52 denote D/A converters, and 53 denotes a circuit for specifying the number of adding operations which supplies the clock pulses and adds the number of the pulses and stores the number. Accordingly, the image signal from the sensor 10 is divided by the sampled number in the divider circuit 48 to produce the average level in the form of digital signal. This signal is multiplied by the constants $K_1$ and $K_2$ in the multiplier circuits 49 and 50, respectively, the outputs of which are converted to analog signals by the D/A converters 51 and 52 to produce the threshold signals $V_a$ and $V_b$.

Figure 9:
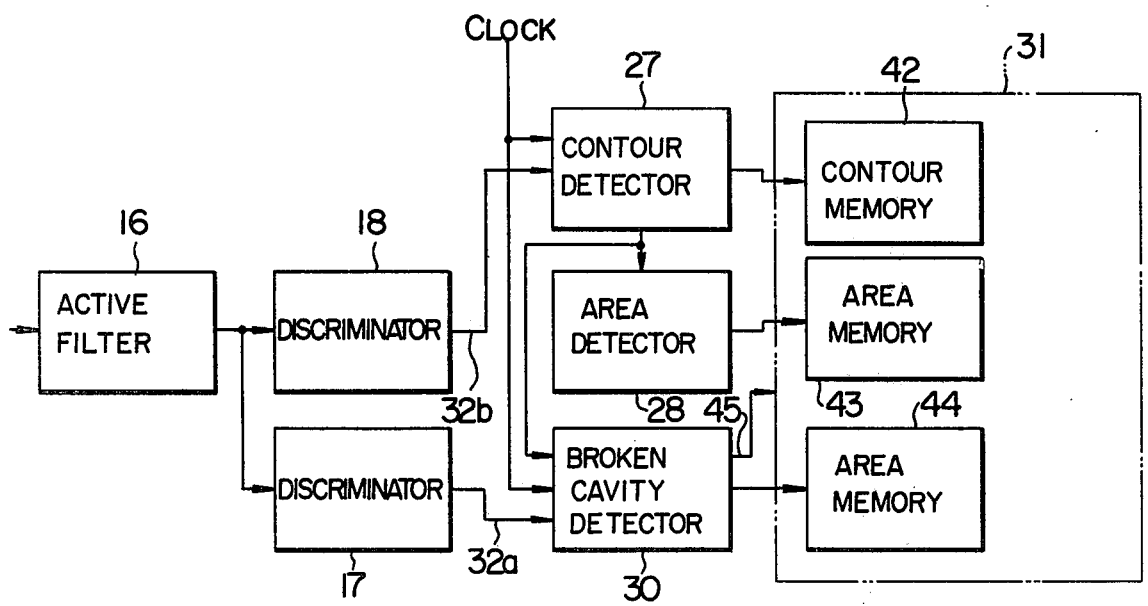
FIG. 9 shows detail of a determination logic shown in FIG. 3.
Figure 11:
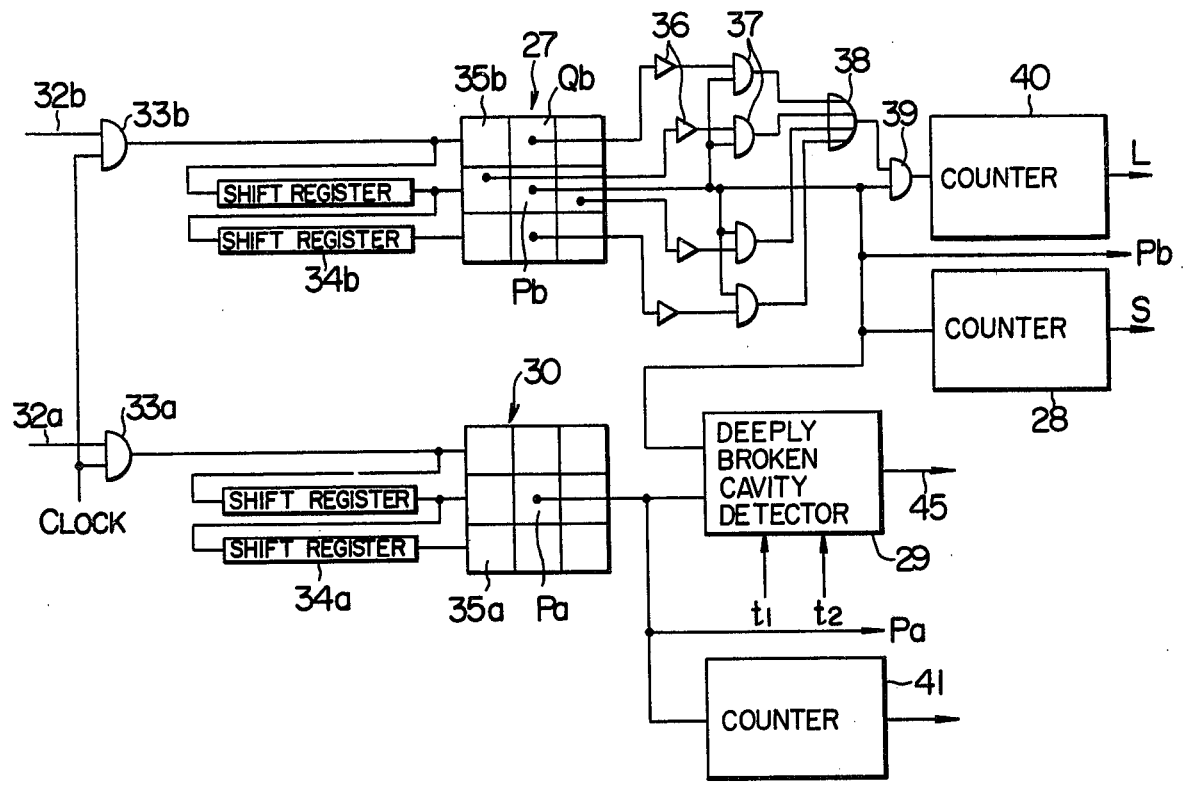
FIG. 11 shows detail of contour detection circuit, area detection circuit and broken cavity detection circuit shown in FIG. 9.

Referring to FIG. 9 and FIG. 11, detail of the determination logic 19 is explained. Numeral 27 denotes a contour detection circuit and 28 denotes an area detection circuit. They determine the length L of the contour and the area S, respectively, of the pattern over entire raster derived from the signals discriminated by the threshold $V_b$ in the discrimination circuit 18. As shown in FIG. 12, the contour detection circuit 27 comprises a gate circuit 33b which gates the clock pulse to quantitize the discriminated signal 32b, a shift register 34b which stores a raster of quantitized discriminated signals while shifting them, an extraction circuit 35b for extracting 3×3 picture elements to examine the relation between the center picture element and the peripheral picture elements, AND circuits 37 each for comparing the signals of the peripheral picture elements $Q_b$, which have been inverted by inverters 36, with the signal of the center picture element $P_b$ to produce "1" signal when they are all "1", an OR circuit 38 for ORing the outputs of the AND circuit 37, an AND circuit 39 for ANDing the output of the OR circuit 38 and the signal of the center picture element $P_b$, and a counter 40 for counting "1" outputs from the AND circuit 39. Accordingly, when the center picture element $P_b$ is "1" and any of the peripheral picture elements $Q_b$ is "0", the AND circuit 39 produces "1" output indicating the contour. This contour signal is counted by the counter 40 for one pattern on one scan line (raster). As the content of the counter 40 is sequentially scanned, it is added to a contour memory 42 (in a computer 31) at an address corresponding to the pattern number assigned to that pattern. When the scan of the pattern is completed, the content of the contour memory 42 for that pattern number stores the contour L of that pattern. Each of the patterns is numbered and an address of the memory corresponding to the pattern number is specified. A numeral 28 denotes an area counter which counts the number of "1"'s of the center picture element $P_b$ of the extraction circuit 35b over one pattern on one scan line (raster). As the content of the area counter 28 is sequentially scanned, it is added to an area memory 43 at an address corresponding to the pattern number assigned to that pattern. When the scan of that pattern completes, the area memory 43 of that pattern number stores the area S of that pattern.

The computer 31 calculates $|L^2-4\pi S|$ based on the length L of the contour stored in the contour memory 42 and the area S stored in the area memory 43. Note that the circular pattern has a relation of $L^2=4\pi S$. Thus, if the result of the calculation shows $|L^2-4\pi S|<\epsilon$, the defect pattern is determined as the pit and when the result shows $|L^2-4\pi S|\geq\epsilon$, the defect pattern is determined as the crack, where $\epsilon$ is an allowance value which may be set arbitrarily.

A broken cavity detection circuit 30 comprises a gate circuit 33a which gates the clock pulses in synchronism with the contour detection circuit 27 to quantitize the discriminated signal 32a, a shift register 34a which sequentially stores a raster of quantitized discriminated signals while shifting them, and an extraction circuit 35a for extracting 3×3 picture elements. When "1" is detected from the center picture element $P_a$ (that is, when the signal from the center picture element $P_a$ exceeds the threshold $V_a$), the defect pattern is determined as the broken cavity. In addition, when the center picture element $P_b$ of the extraction circuit 35b of the contour detection circuit 27 is "1", (that is, when it exceeds the threshold $V_b$), the defect pattern is determined as a portion of the broken cavity if the following condition is met.

Figure 10A:
FIGS. 10a to 10b show charts for explaining the operation of a deeply broken cavity detection circuit.
Figure 10B:
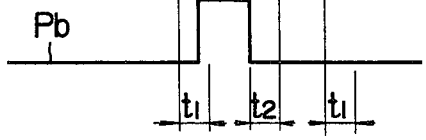

FIGS. 10a to 10b show a method for extracting the broken cavity pattern from the defect patterns discriminated by the threshold $V_b$. FIG. 10a shows the signal discriminated by the threshold $V_a$, of the image signal 26d shown in FIG. 7b, and FIG. 10b shows the signal discriminated by the threshold $V_b$, of the image signal 26d. In the defect pattern discriminated by the threshold $V_b$, if the discriminated signal $P_b$ assumes "1" within a predetermined time $t_1$ from the fall of the discriminated signal $P_a$ or if the discriminated signal $P_a$ assumes "1" within a predetermined time $t_2$ from the fall of the discriminated signal $P_b$ as shown in FIGS. 10a to 10b, the deeply broken cavity detection circuit 29 determines that the defect is a continuous, deeply broken cavity. The deeply broken cavity shown in FIG. 7a does not always exist at the center of the object 13 but it often exists at a corner of the object, as shown in FIG. 7c. In this case, the image signal changes from bright portion to dark portion rather than from bright portion to dark portion and back to bright portion, as shown in FIG. 7b. Accordingly, as described above, when one of the two conditions is met, it is regarded as the deeply broken cavity. Further, since the deeply broken cavity is adjacent to a shallowly broken cavity, the image signal sharply changes from bright portion to dark portion or vice versa in continuous manner. Accordingly, when there exist deeply broken cavity, the both the discriminated signals are detected within the predetermined small time period $t_1$ or $t_2$. In this manner, even if the discriminated signal $P_b$ is below the threshold $V_b$, if it occurs near the discriminated signal $P_b$ which is below the threshold $V_a$, it is determined as the deeply broken cavity.

Numeral 41 in FIG. 11 denotes an area counter which counts the number of picture elements of the discriminated signal $P_a$ which exceeds the threshold $V_a$ over one pattern on one scan line. Each time the content of the area counter 41 is sequentially scanned, it is added to an area memory 44 at an address which corresponds to the pattern number assigned to that pattern. When the scan of that pattern completes, the area memory 44 of that pattern number stores the area of the pattern of the shallowly broken cavity.

It is not always true that one defect pattern always exists on one scan line. Accordingly, the patterns are numbered in the sequence of scan and the information on the area or contour is stored at that address of the memory which is specified by the pattern number. The continuity of the patterns is checked by the serial raster scan and if there is the continuity in the patterns, the same pattern number is assigned and the information is sequentially added and stored in that address of the memory which correspond to the pattern number. If the defect pattern is discontinuous as shown in FIG. 8d, the pattern is divided into three subareas $n_1$, $n_2$ and $n_3$ by lines which intersect two pattern portions in the direction of scan, as shown by dotted lines in FIG. 8d. Since the three sub-patterns are continuous to each other, the same number $n_3$ is assigned to each of the sub-patterns and the information is read out of the memory of the same number and combined together to obtain the information of the respective defect sub-patterns.

In this manner, the broken cavity, crack and pit patterns are classified by the computer 31 and the respective classified patterns are evaluated individually and as a whole to determine the quality of the surface of the object.

Figure 13:
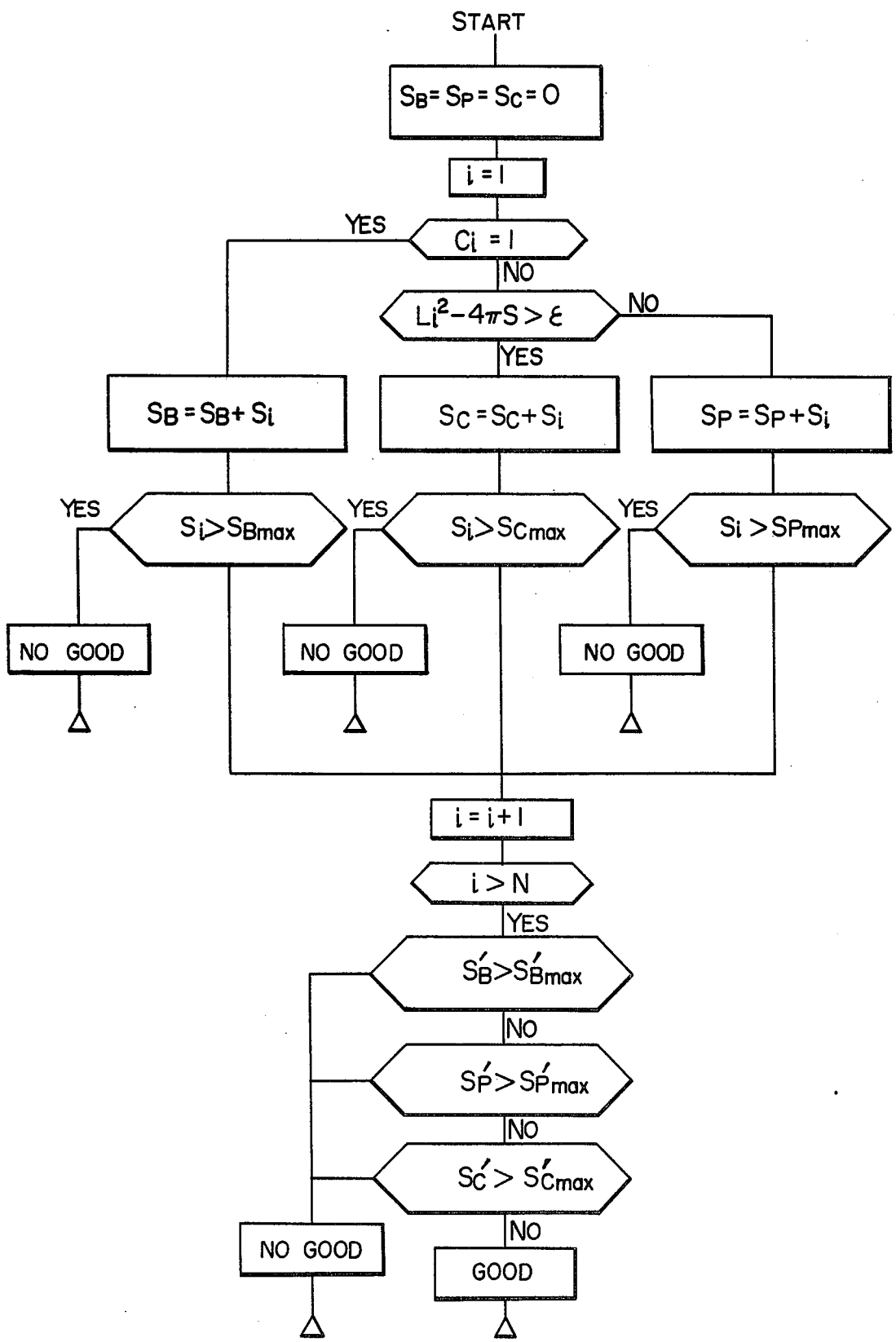
FIG. 13 shows a flow chart in classifying and evaluating the defect patterns by a computer.

The classification and evaluation are carried out in a manner shown by a flow chart of FIG. 13. An initially detected defect pattern is examined for the broken cavity at $C_i=1$ by the signal from the center picture element $P_a$ of the extraction circuit 35a of the broken cavity detection circuit 30 and the output signal 45 from the deeply broken cavity detection circuit 29. If it is determined as the broken cavity, the area $S_B$ of the area memory 43 and the area memory 44 is examined to determine whether it is larger than $S_B$ max which is a reference of no good for one broken cavity. If it is larger, the object is determined as no good, and if it is not larger, the next defect pattern is examined. If the center picture element $P_b$ of the extraction circuit 35b of the contour detection circuit 27 produces a signal while the deeply broken cavity detection circuit 29 does not produce the output signal 45, it is determined as the pit or the crack, and $|Li^2-4\pi Si|$ is calculated using the contour information Li stored in the contour memory 42 and the area information Si stored in the area memory 43, to determine whether the relation $|Li^2-4\pi Si|>\epsilon$ is met. If it is met, it is determined as the crack and the area $S_C$ is examined to determine whether it is larger than $S_C$ max which is a reference of no good for one crack. If it is larger, it is determined as no good, and if it is not larger the next defect pattern is examined. When the relation $|Li^2-4\pi Si|>\epsilon$ is not met, it is determined as the pit and the area $S_p$ is examined to determine whether it is larger than $S_p$ max which is a reference of no good for one pit. If it is larger, it is determined as no good, and if it is not larger the next defect pattern is examined. In this manner, N defect patterns which are distributed over the entire surface of the object are examined, and total area $S'_B$ for all of the broken cavity patterns, total area $S'_p$ for all of the pit patterns and total area $S'_C$ for all of the crack patterns are calculated. Each of the total areas $S'_B$, $S'_p$ and $S'_C$ are then examined to determine whether they exceed $S'_B$ max which is a reference of no good of the broken cavity for total area, $S'_p$ max which is a reference for no good of the pit for the total area and $S'_C$ max which is a reference of no good of the pit for the total area, respectively. If any of them exceeds the references, it is determined as no good and if all of them do not exceed the reference, it is determined as good.

As described hereinabove, the test apparatus of the present invention comprises the illumination means which illuminates collimated lights onto the surface of the object obliquely thereto from at least two opposite directions, a sensor (image pickup device) which picks up the image on the surface of the object from the direction perpendicular to the surface of the object and converts the image to the image signal, the first classification means which determines the image signal as the broken cavity pattern when the image signal exceeds the threshold level which is higher than the average signal level for the surface, the second classification means which determines the image signal as the pit or crack pattern when the image signal does not exceed the threshold level which is lower than the average level, and the determination means which calculates the length L of the contour and the area S of the region in which the discriminated signals are continuous and determines the image signal as the pit pattern when $|L^2-4\pi S|<\epsilon$ (where $\epsilon$ is an allowance value) and determines as the crack pattern when $|L^2-4\pi S|\geq\epsilon$. In this manner, the present apparatus can classify the types of defect and evaluate the defect.

Further, since the sensor (image pickup device) of the present invention uses the one-dimensional or two-dimensional solid state image pickup device or TV camera having the scanning function, the test time can be remarkably shortened.

We claim:
1. A surface defect test apparatus comprising:
an illumination means for illuminating collimated lights onto a surface of an object at a predetermined area including at least a unit picture element, obliquely to said predetermined area from two opposing directions;
a sensor arranged to pick up diffused reflection lights from said predetermined area on said surface of said object in the direction perpendicular to said surface, said sensor having a function to scan the entire surface area of said object;
a first classification means for a defect pattern for said surface as a broken cavity pattern when a bright image signal in an image signal derived from said sensor in response to the diffused reflection light which varies in accordance with a surface condition at each of the picture elements in said predetermined area exceeds a predetermined threshold which is higher than an average level of said image signal;
a second classification means for classifying the defect pattern for said surface as a pit or crack pattern when a dark image signal in said image pattern does not exceed a predetermined threshold which is lower than said average level; and
a discrimination means for discriminating the pit pattern and the crack pattern by a relation between a length of contour and an area of the pattern classified by said second classification means.

2. A surface defect test apparatus according to claim 1 wherein said discrimination means is designed to classify the defect pattern as the pit pattern when a relation $|L^2-4\pi S|<\epsilon$ is met, and classifies as the crack pattern when a relation $|L^2-4\pi S|\geq\epsilon$, where L is the length of the contour, S is the area and $\epsilon$ is an arbitrarily determined allowance value.

3. A surface defect test apparatus according to claim 1, further including means for determining said dark image signal which does not exceed said predetermined threshold which is lower than said average level, as the broken cavity pattern when said dark image signal which does not exceed said lower threshold accompanies said bright image signal which exceeds said predetermined threshold which is higher than said average level, within a predetermined small time period in front of or behind said dark image signal.

* * * * *